United States Patent [19]

Nilsson

[11] Patent Number: 4,794,919

[45] Date of Patent: Jan. 3, 1989

[54] FIXATING DEVICE

[76] Inventor: John S. Nilsson, Brötvägen 18, S-161 39 Bromma, Sweden

[21] Appl. No.: 99,320
[22] PCT Filed: Jan. 30, 1987
[86] PCT No.: PCT/SE87/00043
§ 371 Date: Aug. 25, 1987
§ 102(e) Date: Aug. 25, 1987
[87] PCT Pub. No.: WO87/04612
PCT Pub. Date: Aug. 13, 1987

[30] Foreign Application Priority Data

Jan. 31, 1986 [SE] Sweden .................. 8600437

[51] Int. Cl.$^4$ .................................. A61F 5/04
[52] U.S. Cl. .................. 128/92 YK; 128/92 YV; 128/92 YZ; 128/92 VT
[58] Field of Search .............. 128/69, 80 R, 92 R, 128/92 ZW, 92 Y, 92 YZ, 92 YK, 92 YW, 92 YV, 92 YT, 92 YS, 92 YF

[56] References Cited

U.S. PATENT DOCUMENTS

| | | | |
|---|---|---|---|
| 2,414,882 | 1/1947 | Longfellow | 128/92 YV |
| 2,772,676 | 12/1956 | Pohl | 128/92 YV |
| 3,489,143 | 1/1970 | Halloran | 128/92 YK |
| 4,011,863 | 3/1977 | Zickel | 128/92 YZ |
| 4,055,172 | 10/1977 | Ender et al. | 128/92 VT |
| 4,465,065 | 8/1984 | Gotfried | 128/92 YV |
| 4,483,335 | 11/1984 | Tornier | 128/92 YK |

FOREIGN PATENT DOCUMENTS 1093696 5/1952 France .................. 128/136

Primary Examiner—Robert A. Hafer
Assistant Examiner—Charles H. Sam
Attorney, Agent, or Firm—Young & Thompson

[57] ABSTRACT

A fixating device for fixating a femur fracture in the proximity of the hip joint, comprises an arcuate anchoring arm (17) which is intended to be inserted through an aperture formed in the wall of the femur and down in the femur and brought to an anchoring position therein. The arm merges at one end thereof with a guide part (15) provided with at least one guide hole (24, 25), with a fixating screw to be screwed into the neck of the femur. The anchoring arm (17) terminates in a free end (17A). The guide part (15) has an inwardly facing surface (15B) and an outwardly facing surface (15A), which touch respectively an inner plane (30), and outer plane (29). A center plane 31 lies approximately midway between and is parallel to the inner and outer planes and to the main longitudinal direction of the guide part. The anchoring arm has a convex outer surface tangential to a further plane (32) which is parallel to the other planes. A center part of the anchoring arm lies on one side of the inner plane (30) and the free end (17A) of the anchoring arm lies on the other side of the inner plane (30) and the further plane (32). Thus the convex outer surface and the free end of the anchoring arm are adapted to bear against opposite sides of the interior of a femur at regions spaced along the length of the femur.

3 Claims, 3 Drawing Sheets

FIXATING DEVICE

Field of the Invention

The present invention relates to a fixating device for treatment of fractures of the femur in the vicinity of the hip joint, in particular petrochantera fractures, and being of the kind set forth in the preamble of the following main Claim.

BACKGROUND OF THE INVENTION

The fixating devices used in surgical methods known hitherto require relatively large incisions to be made in the skin of the patient. This prolongs the time required to perform the surgical operation, which commensurately increases the risk of infection.

In the case of one known fixating device it is necessary to penetrate the femur in a number of places, in order to enable a plurality of attachment screws to be inserted. The work entailed herewith is additionally time consuming. Furthermore, the femur is weakened additionally through the number of perforations that need be made therein. This known device comprises a so-called angle plate which has the form of a long plate which is placed along the outside of the femur and attached thereto by means of a multiple of screws which pass through the femur, in holes prepared therein for this purpose.

The upper end of the plate has provided therein at least one guide aperture for receiving a fixating nail or screw. This nail or screw is anchored in the bone tissue within the head of the femur. The major drawback with a device of this kind is that it is necessary to cut and retract a relatively long section of skin, in order to reach all of the plate apertures that are intended to receive through-passing screws. The length of the incision made in the skin is normally longer than the length of the plate.

These many working procedures all contribute in prolonging the time required to perform the operation, which is the primary cause for the increase in the risk of infection. The area of the leg on which the operation is performed is left open and will therefore be exposed to bacterial infection over a correspondingly longer period of time.

In another known operating technique there is used a fixating device which, distinct from the aforedescribed known device, does not require as long an incision in the skin as for the above device. Instead a smaller incision is made and the bone wall is thereafter penetrated in the region of the knee joint. From three to five prebent steel nails having a thickness of about 5 mm and a length of from 40 to 50 cm are then inserted into the aperture thus prepared. These nails are driven up into the femur and out into the bone substance of the femur neck, and from there into the rounded head of the femur. This method requires great skill on the part of the surgeon performing the operation. It is often impossible to avoid wrongful settings in the form of an outward twisting of the bone. Neither is it uncommon for the nails to slide rearwardly and penetrate the skin in the region of the knee joint. This results in sores, which will always become infected. A patient who is operated on in the region of the knee joint will also suffer discomfort at the knee joint in addition to the pain experienced from the broken hip joint.

The French Patent Specification No. 1 093 696 teaches a fixating device which comprises two separate parts. A first part of this device comprises a U-plate which is intended to lie against the femur at a relatively long distance from the femur neck and on the opposite side of the bone in relation thereto. The plate is terminated at its upper end with a guide sleeve which extends obliquely upwards and which is intended to accommodate a friction bolt, which is screwed into the neck of the femur. The plate has positioned therein a shank, which is secured to the plate with the aid of a screw. The shank is extended at its other end with a hook which extends through a hole in the plate and in through an aperture formed in the wall of the bone, so as to grip around the defining edge of said hole, with the pointed end of the hook penetrating into the inside of the bone wall. This device is both complicated and expensive to manufacture, and takes considerable time to place in position. Furthermore, it does not support a fractured femur satisfactorily.

OBJECT OF THE INVENTION

A primary object of the present invention is therefore to provide a fixating device of the aforesaid kind which can be fitted more quickly than the devices known hitherto, therewith shortening the time required to perform such operations.

BRIEF SUMMARY OF THE INVENTION

This is made possible with a fixating device constructed in accordance with the invention and having the characteristic features set forth in the following main claim.

As with the aforesaid known device that use long nails, only one opening need be made in the bone when using the fixating device according to the invention, although in the present case this opening is made in the vicinity of the neck of the femur, instead of in the vicinity of the knee joint. Instead of requiring a relatively large incision to be made in the skin, as in the case of the known device, only two relatively small skin incisions need be made when using the inventive device, the combined lengths of these two incisions being always shorter than the length of the main incision made when using the known device. The fixating device, or fixator, according to the present invention comprises two major parts, which are formed integrally with one another and of which one consists of a guide part which incorporates at least one fixating-screw guide hole and which, when the device is in use, is intended to lie against the outer surface of the bone in a region thereof located in the extension of the neck of the femur when a fixating screw is inserted through a respective guide hole and anchored in the bone tissue of the femur neck. The other major part of the device comprises a relatively long, slightly arcuate anchoring arm which can be inserted through one insertion aperture formed in the bone wall and brought to an anchoring position within the femur, in which position the arcuate anchoring arm lies supportingly against the inner surface of the bone wall at a location approximately midway along the length of the arm and also at a further location at which the end of the arm lies supportingly against the opposite of the bone wall. The anchoring arm is thus able to take-up loads placed thereon in a simple and effective manner.

A drill for drilling a small hole in the bone wall is inserted through a first, relatively small, lower skin incision. The hole is then widened to form an obliquely and downwardly extending aperture in the bone wall, below the region of the bone wall that lies in the extension of the femur neck, using herefor an instrument which is inserted through a second relatively small, upper incision made in the skin. The anchoring arm can now be inserted through the upper incision and through the insertion aperture formed in the bone, so that the arm is pressed down into the anchoring position, wherewith the aforesaid guide part of the device will lie outside the bone aperture at a location adjacent the outer surface of the bone, and serves as a guide for the insertion of one, usually two fixating screws into the neck of the femur. The operation can therefore be performed quickly. The small incisions of the skin can be readily sewn together, whereas not all of the layers of muscle need be sewn together.

BRIEF DESCRIPTION OF THE DRAWINGS

These and other characteristic features of the invention, together with advantages afforded thereby, will be made more apparent in the following description, which is made with reference to an exemplifying embodiment of a fixating device according to the invention illustrated in the accompanying drawings.

DETAILED DESCRIPTION OF THE INVENTION

Figure 1:
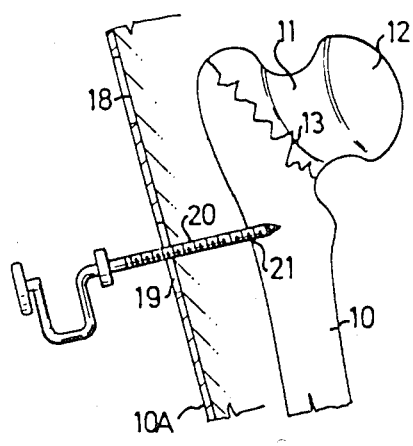
FIGS. 1-4 illustrate schematically various surgical procedures which are carried out when performing an operation in which the fixating device according to the invention is used.

FIG. 1 illustrates schematically a femur 10 and shows the neck 11 of the femur and also the rounded head 12 thereof. In the illustration presented by the Figures it is assumed that a petrochantera fracture 13 is to be fixated with the aid of the fixating device 14 illustrated in FIG. 5. This device consists of a guide part 15, a transition or junction 16, and an anchoring arm 17. The operation is begun by making initially two relatively short incisions 18, 19 in the skin A and retracting the skin in these regions, in accordance with the FIG. 1 illustration.

A drill 20 is then inserted through the lower incision 19, and a hole 21 is drilled in the bone.

Figure 2:
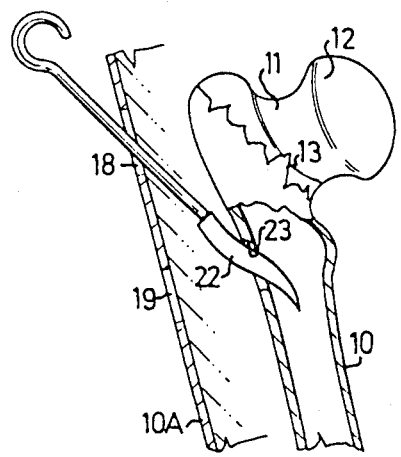

As illustrated in FIG. 2, an instrument 22 is then inserted through the upper incision 18 and moved obliquely down into the hole 21, whereafter the instrument is rotated about its long axis in a manner to widen the hole and form an oblique, downwardly extending insertion aperture 23.

Figure 3:
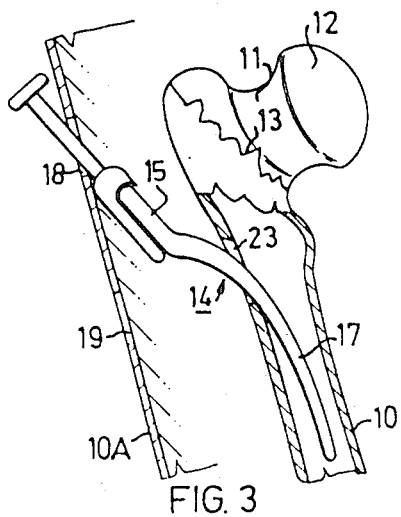
Figure 4:
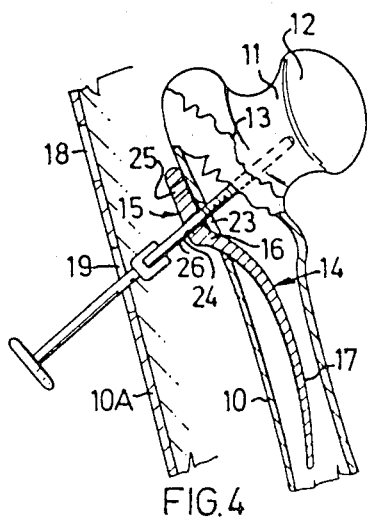

FIG. 3 illustrates the insertion of the inventive fixating device through the upper skin incision 18 and down into the aperture 23, such that the anchoring arm 17 is guided down in the femur to the anchoring position illustrated in FIG. 4.

When the device according to the invention is located in the position illustrated in the Figure, the anchoring arm 17 is located in its anchoring position and the junction part or transition part 16 of the device is located approximately in the insertion aperture 23. The guide part 15 of the device lies outside the wall of the bone. The guide part has provided therein two guide holes 24, 25 for receiving fixating screws 26, of which one 26 is shown in the process of being screwed into the neck of the femur.

The small retracted sections of skin at 18, 19 are sewn together subsequent to having screwed in the screw 16. The guide holes 24, 25 are formed in a manner which will permit the guide part and the screws 26 to move relative to one another in the longitudinal direction of the screws.

Figure 5:
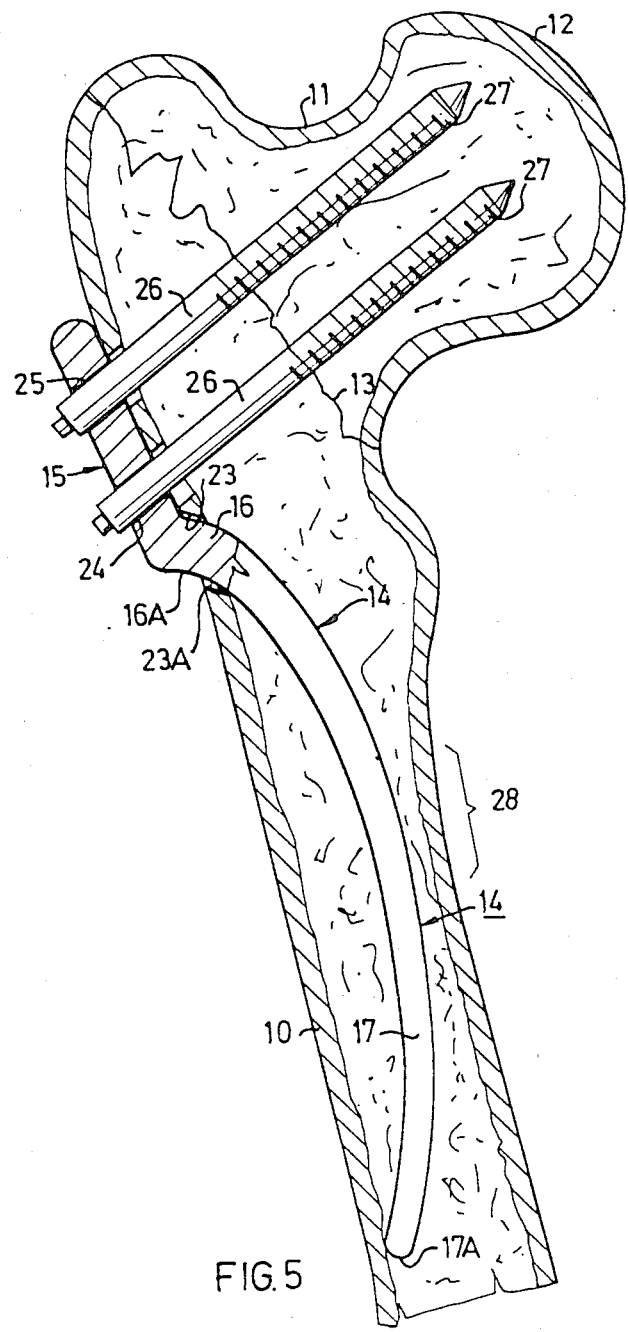
FIG. 5 is an enlarged sectional view of the device according to the invention, and shows the device fitted to the femur of a patient.

FIG. 5 illustrates the fixating device shown in FIG. 4 in larger scale, with two fixating screws 26 screwed into the neck of the femur. The arcuate anchoring arm 17 is gently curved through a relatively large radius of curvature R (FIG. 6), in order to facilitate insertion of the arm through the aperture 23 formed in the bone, and down into the bone, so as to afford a better support against the surrounding bone tissue in the anchoring position of the arm. The junction part 16 of the device presents a shoulder or abutment 16A which has a support surface that adjoins the inside of the arm 17 via a curved transition or junction portion which has a smaller radius of curvature r than the radius of curvature R. The guide section 15 may have any desired form, but is preferably in the form of a relatively thick arm, in accordance with the illustrated embodiment. The guide part 15 has provided therein two guide holes 24, 25 through which the screw-threaded end parts 27 of the screws are inserted the smooth shank surfaces of these screws being guided relatively accurately in the holes 24, 25 when screwing in the screws 26.

As will be seen from FIG. 5, the shoulder or abutment 16A is supported against the defining edge 23A of the insertion aperture 23, when the guide part 15 of the device abuts the outside of the bone and supports thereagainst. The anchoring arm 17 extends downwardly in the bone in a gentle arc, and supports against the bone tissue and the inside of the bone at a location 28 which is approximately midway along the length of the arm. Because the arm 17 is at least twice the length of the guide part 15, and preferably many times longer as in the illustrated embodiment, the distances between the supporting locations of the various parts of the device will be relatively large, thereby providing long mechanical lever arms and good stability.

As will be seen from FIGS. 6-9, the guide part 15 comprises a short thick arm which has approximately the same width and thickness as the anchoring arm 17 and which is formed integrally with said arm, normally made of stainless steel.

The side edges and ends of the guide part 15 and the anchoring arm 17 are fully rounded, as illustrated by the Figures.

Figure 6:
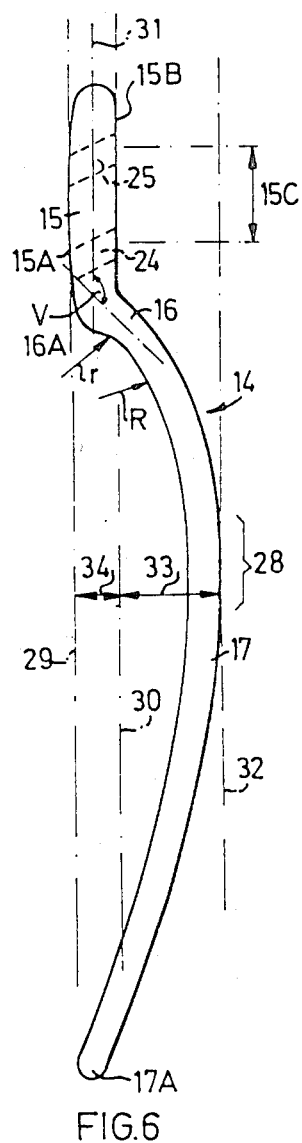
FIG. 6 is a separate end view of the device.
Figure 7:
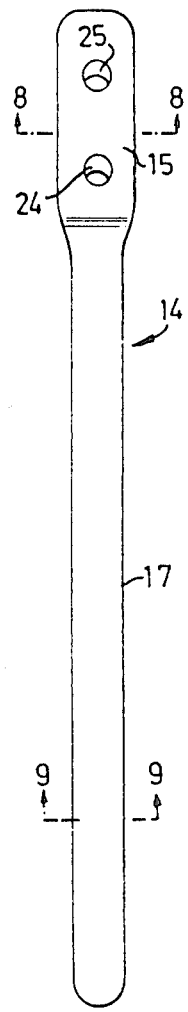
FIG. 7 is a plan view.
Figure 8:
FIG. 8 is a sectional view taken on the line 8—8 in FIG. 7.
Figure 9:
FIG. 9 is a sectional view taken on the line 9—9 in FIG. 7.

In order to enable definition of the particular configuration of the guide part 15 and the anchoring arm 17 there has been drawn in FIG. 6 a plane 29 which touches upon, or is tangential to, the outside 15A of the guide part, and a plane 30 which touches upon, or is tangential to, the inside 15B of the guide part and extends parallel with the plane 29 and also with the center plane 31 of said section, this center plane lying approximately midway between the planes 29, 30 and extending substantially parallel with the main longitudinal direction of the guide section. In addition, there has also been drawn in the Figure a plane 32 which extends parallel with the aforesaid planes 29, 30 and which touches upon, or is tangential to, the convex outer side of the arm 17. As will be seen from FIG. 6, the distance 33 between the planes 30 and 32 is greater than, approximately twice as great as the distance 34 between the planes 29 and 30, i.e. a distance which is approximately equal to twice the thickness of the arm 17 and the guide part 5. The center part of the arm 17 lies on one side of the plane 30, whereas the end 17A of the arm lies on the other side of said plane and in the proximity of the plane 29. The angle V subtended by the center plane 31 of the guide section 15 and the end part of the arm 17 at the junction 16 suitably has a value of from 120° to 145°, and in the illustrated embodiment is about 135°.

In order for the arm 17 and the guide section 15 to form a rigid unit, it is necessary for the arm and the guide section to have substantial thickness. Furthermore, the thickness of the guide section must be such as to enable the guide holes 24, 25 to be given an extension which will enable the screws 26 to be guided in a satisfactory manner.

I claim:

1. A fixating device for fixating a femur fracture in the proximity of the hip joint, comprising an arcuate anchoring arm (17) which is intended to be inserted through an aperture formed in the wall of the femur and down in the femur and brought to an anchoring position therein, said arm merging at one end thereof with a guide part (15), said guide part being provided with at least one guide hole (24, 25), with a fixating screw received in said guide hole, said screw being adapted to be screwed into the neck of the femur, said anchoring arm (17) terminating in a free end (17A) opposite to said one end; said guide part (15) forming an extension of the anchoring arm; said guide part (15) being provided with an inwardly facing surface (15B) and an outwardly facing surface, said inwardly facing surface touching an inner plane, said outwardly facing surface touching an outer plane which is parallel with the inner plane, a center plane lying approximately midway between the inner and outer planes and extending substantially parallel with the main longitudinal direction of the guide part; said anchoring arm being provided with an outer surface which is convex and which is tangential to a further plane (32) which is parallel with said inner and outer planes; said anchoring arm being provided with a center part between said one end and said free end which lies on one side of the inner plane (30), said free end (17A) of the anchoring arm lying on the other side of said inner plane a distance less then the distance (33) between the inner plane (30) and the further plane (32), the distance (33) between the inner plane (30) and the further plane (32) of the anchoring arm being greater than the distance (34) between said inner plane and the outer plane (29) of the guide part, whereby said convex outer surface and said free end of the anchoring arm are adapted to bear against opposite sides of the interior of a femur at regions spaced along the length of the femur.

2. A device according to claim 1, in which said free end (17A) is disposed in the vicinity of said outer plane (29).

3. A device according to claim 1, in which the distance (33) between the inner plane (30) and the further plane (32) is about twice the distance (34) between the inner plane (30) and the other plane (29).

* * * * *